(12) United States Patent
Shen et al.

(10) Patent No.: US 9,849,180 B2
(45) Date of Patent: Dec. 26, 2017

(54) LONG-ACTING SEMI-SOLID LIPID FORMULATIONS

(71) Applicants: Hui Rong Shen, Bothell, WA (US); Na Gan, Bothell, WA (US)

(72) Inventors: Hui Rong Shen, Bothell, WA (US); Na Gan, Bothell, WA (US)

( * ) Notice: Subject to any disclaimer, the term of this patent is extended or adjusted under 35 U.S.C. 154(b) by 0 days.

(21) Appl. No.: 14/853,776

(22) Filed: Sep. 14, 2015

(65) Prior Publication Data

US 2016/0074513 A1 Mar. 17, 2016

Related U.S. Application Data

(60) Provisional application No. 62/050,598, filed on Sep. 15, 2014.

(51) Int. Cl.

| | | |
|---|---|---|
| *A61K 47/00* | (2006.01) | |
| *A61K 47/06* | (2006.01) | |
| *A61K 47/12* | (2006.01) | |
| *A61K 47/14* | (2017.01) | |
| *A61K 31/439* | (2006.01) | |
| *A61K 31/573* | (2006.01) | |
| *A61K 31/5415* | (2006.01) | |
| *A61K 31/519* | (2006.01) | |
| *A61K 31/215* | (2006.01) | |
| *A61K 9/06* | (2006.01) | |
| *A61K 9/00* | (2006.01) | |
| *A61K 31/00* | (2006.01) | |

(52) U.S. Cl.
CPC ............ *A61K 47/14* (2013.01); *A61K 9/0019* (2013.01); *A61K 9/06* (2013.01); *A61K 31/00* (2013.01); *A61K 31/215* (2013.01); *A61K 31/439* (2013.01); *A61K 31/519* (2013.01); *A61K 31/5415* (2013.01); *A61K 31/573* (2013.01); *A61K 9/0051* (2013.01)

(58) Field of Classification Search
CPC ...... A61K 47/14; A61K 9/0019; A61K 31/00; A61K 31/215; A61K 31/439; A61K 31/519; A61K 31/5415; A61K 31/573; A61K 9/06
USPC ....... 514/179, 226.5, 259.41, 299, 330, 530, 514/785, 786
See application file for complete search history.

(56) References Cited

U.S. PATENT DOCUMENTS

| | | |
|---|---|---|
| 4,079,038 A | 3/1978 | Choi et al. |
| 4,093,709 A | 6/1978 | Choi et al. |
| 4,131,648 A | 12/1978 | Choi et al. |
| 4,138,344 A | 2/1979 | Choi et al. |
| 4,180,646 A | 12/1979 | Choi et al. |
| 4,304,767 A | 12/1981 | Heller et al. |
| 4,946,931 A | 8/1990 | Heller et al. |
| 9,271,950 B2 * | 3/2016 | Bannister .................. A61K 9/08 |
| 2005/0042194 A1 | 2/2005 | Ng et al. |
| 2014/0155485 A1 * | 6/2014 | Bannister .................. A61K 9/08 514/571 |
| 2015/0366967 A1 * | 12/2015 | Shen .................... A61K 31/445 514/330 |

FOREIGN PATENT DOCUMENTS

WO WO 2014/134586 A2 9/2014

OTHER PUBLICATIONS

G. Fetih, "Meloxicam formulations for transdermal delivery: hydrogels versus organogels", 2010, J. Drug Delivery Sci. Technol., 20(6), pp. 451-456.*

Fernandez et al., "In Vitro Digestion of the Self-Emulsifying Lipid Excipient Labrasol® by Gastrointestinal Lipases and Influence of its Colloidal Structure on Lipolysis Rate", 2013, Pharmaceutical Research, vol. 30, Issue 12, pp. 3077-3087.*

Yolles et al.; "Sustained Delivery of Drugs From Polymer/Drug Mixtures"; Polymer News; vol. 1; 1970; p. 9-15.

Packhaeuser et al.; "In situ forming parental drug delivery systems: an overview"; European Journal of Pharmaceutics and Biopharmaceutics; vol. 58 No. 2; 2004; p. 445-455.

International Patent Application No. PCT/US2015/050243; Int'l Search Report and the Written Opinion; dated Nov. 23, 2015; 13 pages.

International Patent Application No. PCT/US2015/050243; Int'l Preliminary Report on Patentability; dated Dec. 13, 2016; 21 pages.

* cited by examiner

*Primary Examiner* — My-Chau T Tran

(74) *Attorney, Agent, or Firm* — Baker & Hostetler LLP

(57) ABSTRACT

What is described is a semi-solid controlled release composition comprising a semi-solid lipid pharmaceutical active agent in a solution or a homogenous suspension, methods of using the composition for treating a disease, and methods of manufacturing the composition.

7 Claims, 7 Drawing Sheets

LONG-ACTING SEMI-SOLID LIPID FORMULATIONS

CROSS REFERENCE TO RELATED APPLICATIONS

This application claims benefit under 35 U.S.C. §119(e) of Provisional U.S. patent application No. 62/050,598, filed Sep. 15, 2014, the content of which is incorporated herein by reference in its entirety.

TECHNICAL FIELD

The semi-solid formulations described herein relate to a semi-solid lipid matrix as a delivery vehicle, and controlled release semi-solid formulations comprising the semi-solid lipid vehicle and pharmaceutically active agents. The semi-solid formulations can be in the form of an injectable or a topical formulation for controlled delivery of pharmaceutical active agents, which are useful in the treatment of various types of illness and disease.

BACKGROUND

Pharmaceutical active agents can be administered orally or as an injectable. However, conventional oral and injectable formulations are typically short-acting and often require frequent dosing to maintain a therapeutically effective concentration in the blood stream or at sites where treatment is needed. During the past three decades, controlled drug delivery technologies have been developed to control the rate and period of drug delivery and target specific areas of the body for treatment. Controlled drug delivery technologies offer a number of advantages such as prolonged and improved efficacy, decreased dosing frequency, reduced peak-valley plasma concentration fluctuations, decreased side effects, site-specific delivery, ease of administration, patient compliance, and cost reduction. Although oral drug delivery is the most frequently used route of drug administration, parenteral drug delivery is a preferred route for rapid action. Drug products are administered by implantation, or by subcutaneous, intramuscular, or intraperitoneal injection.

Sustained release or controlled release pharmaceutical drug products have also been developed, e.g., by microencapsulation such as microspheres, microparticles, or implants. A drug delivery vehicle most often consists of a polymeric matrix from which drug is released by diffusion from the matrix and/or by degradation of the matrix.

The earliest drug delivery systems (for the delivery of therapeutic agents) were based on a synthetic biodegradable polymer, polylactic acid (Yolles et al., Polymer News, 1:9-15 (1970)). Numerous other polymers have been described for use in biodegradable/bioerodible matrices for controlled release of active agents. U.S. Pat. Nos. 4,079,038, 4,093,709, 4,131,648, 4,138,344, 4,180,646, 4,304,767 and 4,946,931 describe various types of biodegradable/bioerodible polymers for the controlled delivery of active agents. Although many of these polymers are in the form of semi-solid, however, these semi-solid polymers are often very sticky, and thus the formulations prepared cannot be easily injected.

While the above systems are useful, their manufacture processes are complicated, cumbersome and expensive. In addition, they are often associated with an initial higher release of drug immediately after injection followed by inconsistent drug release kinetics, thus lack of reliability in therapeutic effects in animal studies and human trials.

SUMMARY

One aspect of the description herein is a pharmaceutical composition, comprising a semi-solid gel consisting of one or more glycerides having a structure selected from formulas I, II, III, IV, V, or VI

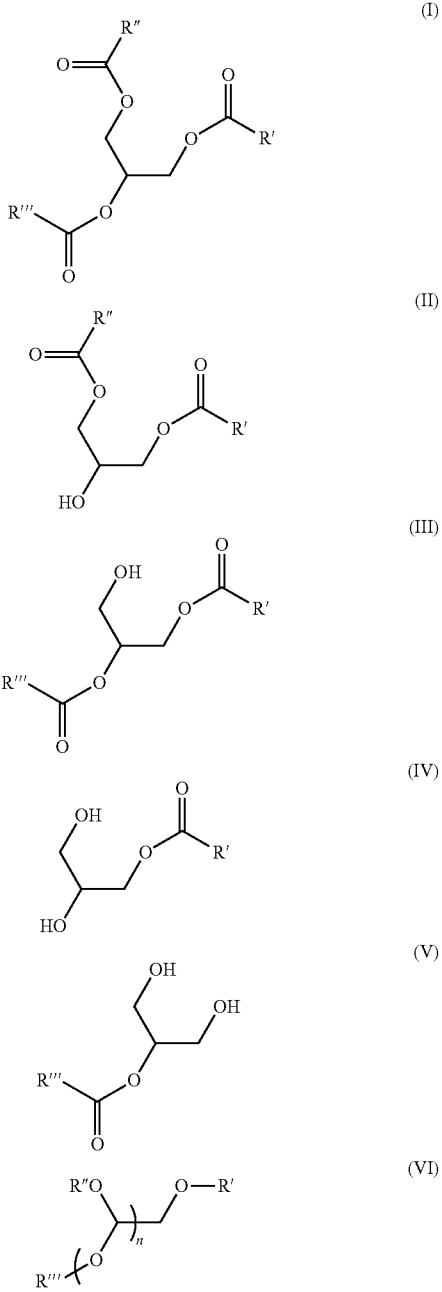

in which R', R", and R''' are alkyl chains independently consisting of a saturated natural fatty acid comprising 8 to 22 carbon atoms, a naturally occurring unsaturated fatty acids comprising 16 to 22 carbons, a non-toxic organic dicarboxylic acid comprising 6 to 10 carbon atoms, or a naturally occurring omega saturated or unsaturated hydroxy acid, in which n is 1 to 10; in which the mixture of glycerides comprise at least two different alkyl chains, and in which the mixture of glycerides is at a concentration of 40 to 99 wt % of the pharmaceutical composition;

an active ingredient at a concentration of 0.01 to 60 wt % of the semi-solid gel, in which a dose of the pharmaceutical composition comprises an amount of the active ingredient effective to treat a subject in need thereof, in which the active ingredient is fully solubilized or homogenously dispersed in the semi-solid gel;

a first excipient consisting of one or more glycerides having a structure selected from formulas I, II, III, IV, or V, in which the first excipient is fully miscible in the semi-solid gel and modifies release kinetics of the active ingredient from the semi-solid gel so that the desired controlled release kinetics and duration of several days to 4 months of the active ingredient from the pharmaceutical composition was achieved when measured in vitro at 37° C.; and a second excipient consisting of one or more glycerides having a structure selected from formulas I, II, III, IV, or V, in which the second excipient is fully miscible with the semi-solid gel, in which the second excipient modifies the viscosity of the pharmaceutical composition to 20 to 2000 cPs at 30° C.;

in which the pharmaceutical composition consists of a homogeneous, single phase semi-solid dosage form or a homogenous semi-solid suspension dosage form suitable for injection into the subject.

In one embodiment of the pharmaceutical composition, the active ingredient is a unit dose of an anti-inflammatory agent, an ophthalmic drug, an antipsychotic, a 5-HT3 antagonist, or a glaucoma drug, for administration to a site in a subject in a pharmaceutically effective amount. The active ingredient preferably is a compound selected from meloxicam, loteprednol, risperidone, granisetron, or latanoprost, or a fatty acid complex thereof.

In another embodiment of the pharmaceutical composition, the semi-solid gel comprises polyglyceryl-2-diisostearate, SOFTISAN® 378, SOFTISAN® 645, or SOFTISAN® 701.

In another embodiment of the pharmaceutical composition, the first excipient comprises SOFTISAN® 701, SOFTISAN® 378, GELUCIRE®39/01, SUPPOCIRE® A, or SOFTISAN® 138, and adjusts the rate of release of the active ingredient from the pharmaceutical composition. The first excipient may have a lower or higher HLB (hydrophobicity) than the semi-solid gel. The first excipient preferably is at a concentration of 0 to 30 wt % of the pharmaceutical composition In another embodiment of the pharmaceutical composition, the second excipient comprises SOFTISAN® 701, SOFTISAN® 378, GELUCIRE® 39/01, SUPPOCIRE® A, or SOFTISAN® 138, and functions to decrease the viscosity of the pharmaceutical composition. The second excipient preferably is at a concentration of 0 to 30 wt % of the pharmaceutical composition.

In another embodiment of the pharmaceutical composition, the active agent is a unit dose of an anti-inflammatory agent, an ophthalmic drug, an antipsychotics, a $5\text{-HT}_3$ antagonist, or a glaucoma drug for administration to a site in a subject in an amount effective to achieve their therapeutic efficacy at the site or systemically. The active agent preferably is at a concentration of 0.01 to 60 wt %, and more preferably at a concentration of 3 to 40 wt %. The active agent is selected from the drugs consisting of meloxicam, loteprednol, risperidone, granisetron, or latanoprost, or a fatty acid complex thereof.

Another embodiment of the description herein, is a method for preventing or treating a disease or disorder comprising administering to a subject in need thereof the pharmaceutical composition. The pharmaceutical composition may consist of an injectable or a topical semi-solid formulation, which is administered by injection by a 21 gauge to 27 gauge needle. Administration may be by subcutaneous, intramuscular, intraperitoneal injection, or by injection at the site of surgery. Administration can also be by topical application to skin or a mucous membrane.

Another aspect of the description herein is method of manufacturing the pharmaceutical composition, comprising selecting an active agent in a dosage amount sufficient to effectively treat a patient; fully solubilizing or homogeneously mixing the active agent in a semi-solid gel consisting of one or more glycerides having a structure selected from formulas I, II, III, IV, V, or VI

(I)

(II)

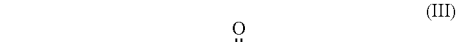

(III)

(IV)

(V)

-continued

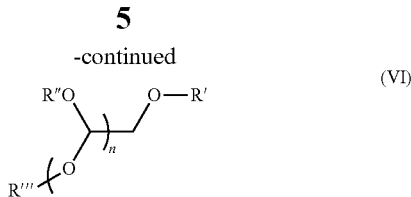

in which R', R", and R''' are alkyl chains independently consisting of a saturated natural fatty acid comprising 8 to 22 carbon atoms, a naturally occurring unsaturated fatty acids comprising 16 to 22 carbons, a non-toxic organic dicarboxylic acid comprising 6 to 10 carbon atoms, or a naturally occurring omega saturated or unsaturated hydroxy acid, in which n is 1 to 10; in which the mixture of glycerides comprise at least two different alkyl chains, in which the concentration of the active agent is 0.01 to 60 wt % of the semi-solid gel;

measuring the release kinetics of the active agent from the semi-solid gel resulting from step ii to determine if the desired controlled release kinetics and duration of several days to 4 months of the active ingredient from the semi-solid gel was achieved when measured in vitro at 37° C.;

adding a first excipient to the semi-solid gel resulting from step ii, in which the first excipient consists of one or more glycerides having a structure selected from formulas I, II, III, IV, or V, having a comparable HLB number than the semi-solid gel, in which the first excipient is fully miscible in the semi-solid gel and at a concentration sufficient to slow the release of the active agent from the semi-solid gel to achieve the desired controlled release kinetics and duration of several days to 4 months is at a concentration of 0 to 30 wt % of the pharmaceutical composition;

measuring the viscosity of the semi-solid gel containing the active ingredient resulting from step iv to determine if the viscosity is less than 2000 cPs at 30° C.; and adding a second excipient to the semi-solid gel resulting from step iv, in which the second excipient consists of one or more glycerides having a structure selected from formulas I, II, III, IV, or V, in which the second excipient is fully miscible with the semi-solid gel, in which the second excipient modifies the viscosity of the pharmaceutical composition to 20 to 2000 cPs at 30° C.;

in which the resulting pharmaceutical composition consists of a homogeneous, single phase semi-solid dosage form or a homogenous semi-solid suspension dosage form.

In one embodiment of the method of manufacturing the pharmaceutical composition, the desired controlled release kinetics and duration (several days to 4 months) of the active ingredient from the pharmaceutical composition was achieved when measured in vitro at 37° C., further comprising selecting a free base or a salt form of the active ingredient to slow its release rate from the semi-solid gel

DETAILED DESCRIPTION OF ILLUSTRATIVE EMBODIMENTS

Figure 1:
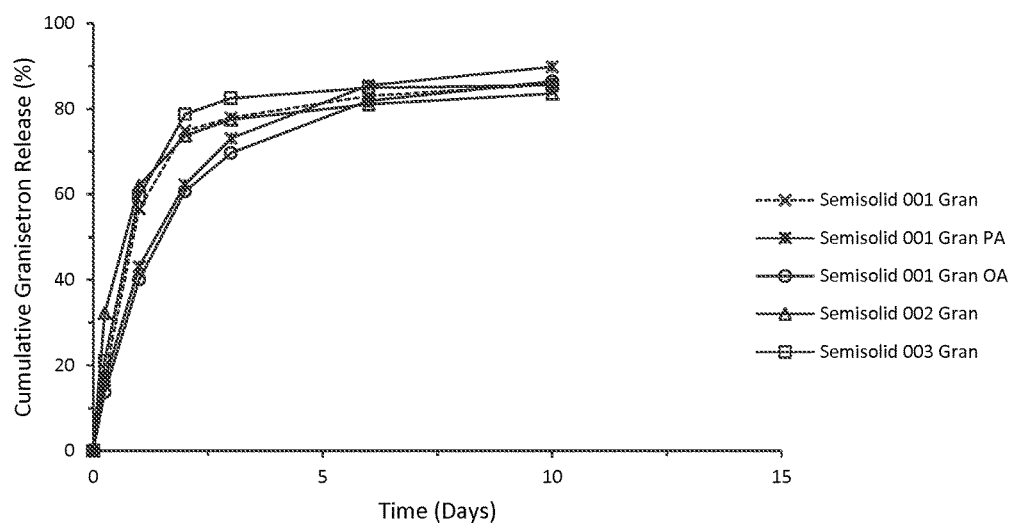
FIG. 1 shows granisetron release from different semi-solid compositions containing a main semisolid lipid carrier and a modifying excipient: semisolid 001 Gran: [S701/Sup A (75/25)]/granisetron (96/4); semisolid 001 Gran PA: [S701/Sup A (75/25)]/granisetron PA (93/7); semisolid 001 Gran OA: [S701/Sup A (75/25)]/granisetron OA (93/7); semisolid 002 Gran: [PGDS/Sup A (70/30)]/granisetron (96/ 4); and semisolid 003 Gran: [S645/Sup A (80/20)]/granisetron (96/4), all in 25 mM phosphate buffered saline, pH 7.4, 37° C.

Advantages of Bioerodible Semisolid Depot Technology
Biocompatible and Bioerodible Semi-Solid Lipid Depot Containing Active Drugs The semi-solid formulations described herein provide a prolonged period of drug release such that therapeutic concentrations of the drug are achieved rapidly and maintained for several days up to four months. The potential benefit of the prolonged release profile is to achieve rapid drug action, maintaining higher levels of active drug at the site where treatment is needed over time to potentially provide greater therapeutic effect.

One of the benefits of bioerodible, semisolid depot technology is that no significant initial burst is found in the formulations described herein. Typically, controlled release injections are associated with an initial burst (higher release of drug immediately after injection). In vitro drug release and animal studies have shown that injectable composition based on the bioerodible semisolid depot technology described herein produce less post-injection burst that is typically associated with other commercially available injectable controlled release technologies. For example, NUTROPIN® (somatropin of rDNA origin for injection) has a drug release profile of huge burst followed by very slow drug release.

Drug concentration in the semisolid depot technology described herein can be considerably greater than what is typical with other controlled release technologies. For example, a long-acting mepivacaine has been developed using this semi-solid drug delivery technology in which only about 3 wt % of mepivacaine can to be loaded into the polyorthoester vehicle due to the drug's low solubility in the vehicle.

The semisolid depot formulations exhibit described herein have very low viscosity, about 10,000 mPa·s or less at 30° C., preferably 1000 mPa·s or less. Therefore, they can be injected through a small needle such as 23 gauge or even 25 gauge needles, and will exhibit minimal pain (similar to aqueous solution injection) during injection. Additionally, since the semisolid formulations described herein have a higher capacity for drug loading, less volume of drug product is required to be injected. Small injection volumes and low viscosity semi-solid formulations result in easier and less painful administration. Polyorthoester semi-solid formulations have a viscosity of thousands of mPa·s at 30° C., which is difficult to be injected with a 21 gauge needle.

The formulations described herein comprise semisolid lipids that are glycerides of glycerol with natural fatty acids. These compounds are readily hydrolyzed to glycerol and free fatty acids by lipase. These compounds are non-toxic, and exhibit excellent biocompatibility in the body. The formulations described herein are biodegradable, bioerodible, and fully resorbable. In animal studies, at two weeks after dosing, no adverse effect of the semi-solid formulation on wound healing was observed. The administration site appeared to be pinkish, and the rat sciatic nerve appeared to be normal, no inflammation, necrosis, ulceration, or infection was observed.

Compared to microspheres and other polymer-based controlled release injectable systems, the semisolid formulations described herein are readily manufactured at low cost. The active ingredient(s) and semi-solid vehicle components are simply mixed at without the use of solvents at relatively low elevated temperatures. Note that since semi-solid lipid and low-melting point lipid (less than 50° C., and most preferably less than 40° C.) (modifying excipient) are used, the manufacturing process may be at about 60° C.

Further, the formulations described herein can be administered directly for site specific delivery. Since the formulations provide a sustained drug release over a period of days to months resulting in increased duration of pharmacological action, and reduced frequency of drug administration. The formulations also produce reduced side effects (due to local drug delivery) when compared with systemic administration. The ease of use should produce improved patient compliance.

All technical and scientific terms are used herein according to their conventional definitions as they are commonly used and understood by those of ordinary skill in the art of drug delivery. Specific terms for the description herein will be defined below.

Definitions

The term "semi-solid" denotes the physical state of a material that is flowable under a moderate pressure. More specifically, the semi-solid material has a viscosity of less than 10,000 cps (mPa·s) at 30° C. One of the excipient components can have a viscosity of about 5,000 to 6,000 mPa·s. After mixing with a viscosity reducer and active ingredient, the overall viscosity will be reduced to hundreds of cps for the final formulation/drug product.

The term "thixotropic" means a shear thinning property of a fluid or gel material when mixed or agitated. Certain gels or fluids that are thick (viscous) under static conditions will flow (become thin, less viscous) over time when shaken, agitated, or otherwise stressed. They then take a fixed time to return to a more viscous state. Many gels and colloids are thixotropic materials, exhibiting a stable form at rest but becoming fluid when agitated. Thixotropy is the tendency for the viscosity of a liquid to decrease when subjected to shear. Thixotropic Index is the ratio of two viscometer readings. The higher the difference in the two readings, the more thixotropic the material is, and easier to move. The term "thixotropic" is used in its conventional sense to refer to a gel composition that can liquefy or at least exhibit a decrease in apparent viscosity upon application of mechanical force such as shear force. The extent of the reduction is in part a function of the shear rate of the gel when subjected to the shearing force. When the shearing force is removed, the viscosity of the thixotropic gel returns to a viscosity at or near that prior to being subjected to the shearing force. Accordingly, a thixotropic gel may be subjected to a shearing force when injected from a syringe which temporarily reduces its viscosity during the injection process. When the injection process is completed, the shearing force is removed and the gel returns very near to its previous state.

A "thixotropic agent" as used herein is one that increases the thixotropy of the composition in which it is contained, promoting shear thinning and enabling use of reduced injection force.

The term "bioerodible" refers to a material that gradually decomposes, dissolves, hydrolyzes and/or erodes in situ. Generally, the "bioerodible" semi-solid lipids described herein are materials that are hydrolizable, and bioerode in situ primarily through both lipolysis and hydrolysis.

The semi-solid lipids, solvent and other agents of the description must be "biocompatible"; that is they must not cause irritation or necrosis in the environment of use. The environment of use is a fluid environment and may comprise a subcutaneous, subconjunctival, intramuscular, intravascular (high/low flow), intramyocardial, adventitial, intratumoral, or intracerebral portion, wound sites, tight joint spaces or body cavity of a human or animal.

Low-Solubility Semi-Solid Lipids of the Formulation

The semi-solid lipids useful in the formulation described herein are a mixture of one or more monoglycerides, diglycerides, or triglycerides of low water solubility having the structure of I, II, III, IV, V, or low hydrophilic-lipophilic balance (HLB) polyglyceryl esters with the structure of VI

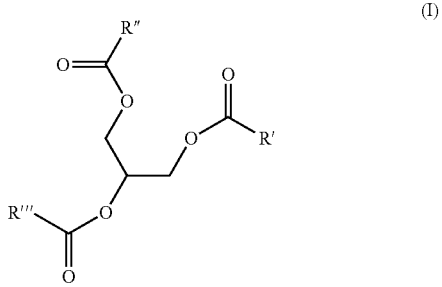

(I)

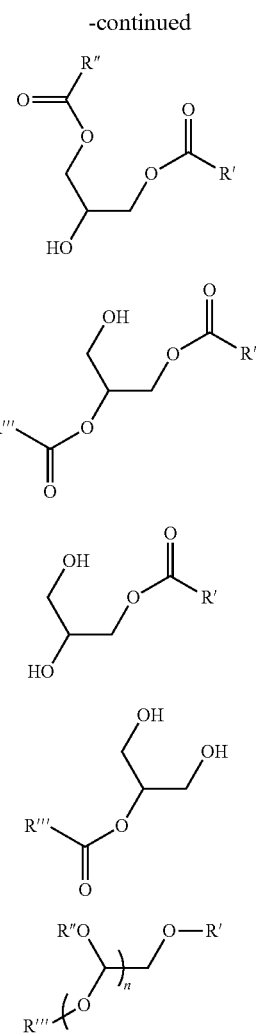

in which R', R", and R'" are independent fatty acid moiety or hydrogen, and n is 1-10. The fatty acids include saturated natural fatty acids containing 8, 9, 10, 11, 12, 13, 14, 15, 16, 17, 18, 19, 20, 21 or 22 carbon atoms, preferably 8-18 carbon atoms, such as caprylic acid, capric acid, lauric acid, myristic acid, palmitic acid, stearic acid, arachidic acid, or behenic acid; or naturally occurring mono-unsaturated fatty acids such as palmitoleic acid, cis-vaccenic acid, or oleic acid; or polyunsaturated fatty acids such as linoleic acid, α-linolenic acid, arachidonic acid, eicosapentaenoic acid, and docosahexaenoic acid; naturally occurring omega saturated and unsaturated hydroxy acids such as 16-hydroxy palmitic acid, 18-hydroxy stearic acid, 2-hydroxy-docosanoic, 15-hydroxy-hexadecanoic acid, 17-hydroxy-octadecanoic acid, 2-hydroxy-oleic acid, 2-hydroxy-linoleic acid, or ricinoleic acid; additional naturally occurring fatty acids such as vernolic acid or furanoid fatty acids; and finally non-toxic organic dicarboxylic acid containing 6, 7, 8, 9, or 10 carbon atoms such as adipic acid, azelaic acid, or sebacic acid which can be used along with other fatty acids. A small portion of these acids can be added to the fatty acid mixtures and react with glycerol to produce the mixed esters.

In addition, polyglyceryl esters with an HLB value of less than 4 and molecular weight of less than 2,000 Dalton, such as polyglyceryl-2-diisostearate (HLB=3.8), polyglyceryl-10-decaoleate (HLB=3.5), or polyglyceryl ester of mixed vegetable fatty acids (HLB=2.5), are also useful semi-solid vehicle.

Triglycerides are typically manufactured through direct esterification of glycerol with defined fatty acid blends and have therefore precise composition and properties regarding melting point, polarity (hydroxyl value), and consistency. Partial glycerides are esters of glycerol with fatty acids, whereby only a part of the existing hydroxyl groups are esterified. Some hydroxyl groups within the glycerol ester are free contributing to the polar properties of the material.

The semi-solid lipids compositions in the present description comprise triglycerides, diglycerides, and monoglycerides of mixed esters in a relatively viscous liquid or paste form with an aqueous solubility of less than 0.1 mg/mL, with an HLB value of not more than 6, preferably less than 5. Glycerides of short-chain fatty acid with aliphatic chains of fewer than six carbons (i.e., butyric acid) and glycerides of medium-chain fatty acids with aliphatic chains of 6, 7, 8, 9, 10, 11 or 12 carbons are typically in the form of mobile liquid and are difficult to form a long-lasting depot in the human body at the body temperature of 37° C. and physiologic pH. Triglycerides of long-chain fatty acids with aliphatic chains 13, 14, 15, 16, 17, 18, 19, 20 or 21 carbons, and very long chain fatty acids with aliphatic chains longer than 22 carbons typically have a higher melting point and are more likely to be a hard waxy solid at room temperature. As the number of fatty acid carbons increases, the solubility of the formed triglycerides decreases in the human body. Therefore, the triglycerides of mixed esters and partial glycerides of fatty acids useful for the formulation described herein are mixed esters containing medium chain fatty acids. Myristic triglyceride, palmitic triglyceride, and stearic triglyceride are in the form of solid powder or flakes with a melting point of 57° C., 63° C. and/or 71° C., respectively. Fatty acids with aliphatic chains of 6, 7, 8, 9, 10, 11 or 12 carbons, which have high polarity and therefore exhibit superior solvent characteristics for active drugs, and long chain fatty acids with aliphatic chains of 13 to 21 carbons which tends to increase melting point and hardness, so a proper mixed esters containing both medium-chain and long-chain fatty acids can be in the physical form of a soft paste.

Commercial mixtures of glycerides are readily available. For example, SOFTISAN® 378 (S378) is a mixture of caprylic/capric/myristic/stearic triglycerides, containing all four types of fatty acids, is an off-white to yellowish soft paste with a drop point of 39° to 42° C., and this material is practically insoluble in water at 20° C. (with a water solubility of less than 0.1 mg/mL). At 40° C., after this material being melted and become a liquid, it has a dynamic viscosity of 30 mPa·s. For this type of glycerides of saturated fatty acids, the medium-chain fatty acids play the role of solubilizing the active ingredient into the semi-solid lipid, while the hydrophobicity/lipophilicity of long-chain fatty acids is a main factor controlling drug release, control the slow erosion/dissolution of semi-solid lipid, and the release of the active ingredient.

Viscosity also plays a role in controlling the release of active ingredients from the semi-solid depot. Other fatty acids such as omega saturated such as hydroxystearic acid (and unsaturated hydroxy acids) which tends to increase viscosity of the material and other non-toxic organic dicarboxylic acid to increase polarity of the material and solubility of the active drugs. These functional groups such as hydroxyl groups (—OH) and carboxylic groups (—COOH), can form intra and intermolecular hydrogen bonding, and can increase the viscosity of the glycerides of saturated fatty acids. They can also form molecular interactions with drug molecules, and contribute to retain the active ingredient inside the semi-solid depot. For example, caprylic/capric/isostearic/hydroxyl-stearic/adipic glycerides is a mixed ester of a relatively viscous yellowish liquid with a viscosity of approximately 6000 mPa·s at 20° C., and this material is practically not soluble in water (with a water solubility of less than 0.1 mg/mL). Introducing hydroxyl-steric fatty acid with hydroxyl groups and adipic dicarboxylic acid with carboxylic groups changes this mixed ester into a high viscosity liquid. When additional hydrophobic stearic acid is introduced, the resulting material (caprylic/capric/isostearic/hydroxylstearic/stearic acid/adipic glycerides) becomes a sticky paste with a viscosity of about 540 mPa·s at 50° C.

Unsaturated glycerides with naturally occurring omega unsaturated hydroxy acids, and monounsaturated and polyunsaturated fatty acids typically have a lower melting point and are more likely to be liquid or soft paste. Some hydroxyl groups within the glycerol ester are free contributing to the polar properties of the material, and potential good solubility of active ingredients. Especially, glycerides of unsaturated hydroxy acids show even better solubility for low solubility active ingredients due to the presence of hydroxyl groups. For example, ricinoleic acid partial glycerides is a white to yellowish paste with a viscosity of approximately 500-600 mPa·s at 30° C., and this material is dispersible in water. Other unsaturated partial glyceride examples are glyceryl oleate, glyceryl linoleate, glyceryl linoleate, glyceryl hydroxyoleate, glyceryl hydroxylinoleate, and glyceryl monooleate linoleate, and glyceryl monooleate. Since these materials contain unsaturated components, interaction with oxygen must be considered. Antioxidant(s) may be added to the material to increase stability.

Polyglyceryl esters are formed chemically by esterification of fatty acids, largely saturated or mono-unsaturated, to one or several hydroxyl groups of polyglycerol with the structural formula, VI:

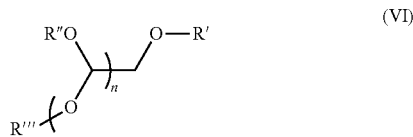

In which the value of n is not more than 10, preferably less than 4, and R', R", and R''' each may be a fatty acid moiety or hydrogen.

Only 30% to 50% of the total amount of hydroxyl groups typically is esterified by fatty acids. Normally, they are used as emulsifying agents due to their amphiphilic characteristics. Almost all the commercially available polyglyceryl esters are relatively hydrophilic, with a high HLB value of greater than 4, and are either soluble in water or dispersible in water. They are used as water additives and products, and are not hydrophobic enough to be used as a controlled semi-solid delivery vehicle.

However, polyglyceryl esters such as polyglyceryl-2-diisostearate (HLB=3.8), polyglyceryl-10-decaoleate (HLB=3.5), polyglyceryl ester of mixed vegetable fatty acids (HLB=2.5), bis-diglyceryl polyacyladipate, diglycerin laurate, diglycerin myristate, diglycerin oleate, and polyglyceryl ricinoleate with an HLB value of not more than 4, preferably less than 3, can be used as a semi-solid vehicle component. They can be used as oil additives due to their low hydrophilic-lipophilic balance value, and are fully compatible with semi-solid lipid vehicle components. They typically exist as a viscous liquid due to the presence of multiple hydroxyl groups, and will become a soft paste when a solid lipid was added as a modifying excipient. The molecular weight of the polyglyceryl esters should be less than 2,000 Dalton, preferably less than 1,500 Dalton, and more preferably not more than 1,000 Dalton. For example, polyglyceryl-2-diisostearate (HLB=3.8) is slightly yellow viscous liquid, when a waxy solid lipid G39/01 (a glyceride of $C_{12}$ to $C_{18}$ fatty acids) is added, the mixture becomes a soft paste. Polyglyceryl-10-decaoleate (HLB=3.5) is a viscous liquid, when a waxy solid lipid G39/01 (a glyceride of $C_{12}$ to $C_{18}$ fatty acids) is added, the mixture becomes a soft paste.

The useful semi-solid lipids (low HLB triglycerides of mixed esters, partial glycerides (including monoglycerides and diglycerides) of fatty acids, and low HLB polyglyceryl esters) should be hydrophobic enough, and have low solubility with an aqueous solubility of less than 1 mg/mL in physiological pH buffer at 37° C., preferably less than 0.1 mg/mL. They are in the form of either a soft paste, or a viscous liquid at room temperature.

The useful main semi-solid lipids alone, the main semi-solid lipid mixed with the modifying excipients (the final delivery vehicle), and the delivery vehicle with the active ingredients can form a defined long-lasting depot once administered into the body at 37° C., and will gradually degrade/erode, and be dissolved into the body liquids, and the semi-solid lipids will eventually be hydrolyzed to natural free glycerol and free fatty acids by lipase through a process called lipolysis.

Modifying Excipients

The modifying excipients suitable for the present description are pharmaceutically acceptable and semi-solid lipid compatible materials. These materials can be in the form of liquid, semi-solid, or solid at room temperature, and are fully compatible with the semi-solid lipid to form a single phase semi-solid delivery vehicle for active drugs.

More specifically, suitable modifying excipients can be also triglycerides of mixed esters and partial glycerides of fatty acids as described in the main semi-solid lipid vehicle. Since these modifying excipients are structurally similar to the main semi-solid lipid vehicle, they are expected to be fully compatible. Physically, these materials can be in the form of liquid, semi-solid, or solid at room temperature, and should also have low solubility with an aqueous solubility of less than 1 mg/mL in physiological pH buffer at 37° C., preferably less than 0.1 mg/mL with an HLB value of not more than 6, preferably less than 5. The modifying excipient is preferably to have comparable solubility as the main semi-solid lipid. If the modifying excipient is too hydrophilic and water soluble, it will cause a significant burst of the active drug(s), especially when the active drugs are relatively soluble, which may cause undesirable side effects. If the modifying excipient is significantly more insoluble than the main semi-solid lipid, it will retain in the body significantly longer when the active drug and the main semi-solid lipid is completely dissolved and resorbed by the body.

The purposes of adding modifying excipients to the main semi-solid lipid vehicle is to modify the release kinetics of the active drugs from the delivery vehicle, to reduce the viscosity of the main lipid vehicle, to modify the texture or consistency of the vehicle, and to ensure the final drug product/formulation remain as a long-lasting well-defined depot to control the gradual release of active drugs. Any one of the three types of the useful semi-solid lipids, triglycerides of mixed esters, partial glycerides of fatty acids, and low HLB polyglyceryl esters, can be used as a modifying excipient, which will be a mixture of two semi-solid lipids. Another type of useful modifying excipient is a solid triglyceride, diglyceride or monoglyceride with a melting point of less than 60° C., preferably around and slightly above body temperature (35° to 50° C.). When the melting point gets too high, it will cause the hardening of the semisolid vehicle during storage, and this solid triglyceride or partial glycerides could retain the body significantly longer. For example, solid triglycerides and partial glycerides with a melting point of around and slightly above body temperature are typically in the form of waxy solid, and can serve as a lubricant (due to the waxy property from the long alkyl chains of fatty acids) that reduces the viscosity of the relatively viscous liquid or paste. For example, a 10 to 20 wt % of a triglycerides of $C_{10}$ to $C_{18}$ fatty acids (S138), hydrogenated cocoglycerides (a different percentage mixture of $C_{10}$ to $C_{18}$ fatty acids with melting points from 25° to 50° C.), glyceryl laurate, glyceryl myristate, glyceryl palmitate, glyceryl monostearate (HLB=5), glyceryl hydroxyl stearate, or a glyceride of $C_{12}$ to $C_{18}$ fatty acids (G39/01, HLB=1) with a melting point of 37° to 40° C., a glyceride of $C_{10}$ to $C_{18}$ fatty acids (SUPPOCIRE® A, HLB=1) with a melting point of 35° to 36.5° C., glyceryl cocoate (glyceryl monococoate, dicocoate or tricoccoate), hydrogenated palm/palm kernel oils (a mixture of monoglycerides, diglycerides and triglycerides with different percentage of $C_{10}$, $C_{12}$, $C_{14}$, $C_{16}$ or $C_{18}$ fatty acids with melting points from 20° to 45° C.), can be added to the relatively viscous yellowish liquid of caprylic/capric/isostearic/hydroxylstearic/adipic glycerides (a mixed ester), and changed the delivery vehicle to a relatively non-viscous soft paste. This could not only make the semi-solid depot a more defined shape in the body, and potentially prolong the drug release duration, but also improve the ability of the semi-solid formulation to be administered by syringe.

The concentrations of modifying excipient in the delivery vehicle may vary. For example, the concentration of the excipient in the vehicle may be in the range of about 1 to 50 wt %, preferably about 5 to 30 wt %, and more preferably about 10 to 20 wt %.

The delivery vehicle of the semi-solid lipid formulation comprises one main semi-solid lipid, and typically one and potentially more modifying excipients selected from those described in the preceding section. The delivery vehicle can be prepared by mixing or blending together the main semi-solid lipid and the modifying excipients homogenously. The mixing and blending can be performed by any methods or using any suitable devices to achieve a smooth homogeneous and non-sticky semi-solid mixture at an elevated temperature without the use of any solvents, or with the help of organic solvents to dissolve the active agents or vehicle components.

Pharmaceutical Semi-Solid Formulations

"Active agent" includes any locally or systemically acting active agents which may be administered to a subject by topical application or by subcutaneous, subconjunctival, intradermal, intramuscular, intraocular, or intra-articular injection. Examples of these agents include, but not limited to, anti-infectives (including antibiotics, antivirals, fungicides such as itraconazole, scabicides or pediculicides), antiseptics (e.g., benzalkonium chloride, chlorhexidine gluconate, nitrofurazone, or nitromersol), steroids (e.g., estrogens, progestins, androgens, or adrenocorticoids), therapeutic polypeptides (e.g., exenatide, octreotide, insulin, erythropoietin, or morphogenic proteins such as bone morphogenic protein), corticosteroids, analgesics and anti-inflammatory agents (NSAIDs) (e.g., aspirin, ibuprofen, naproxen, ketorolac, indomethacin, meloxicam, COX-1 inhibitors, or COX-2 inhibitors), chemotherapeutic and antineoplastic agents (e.g., paclitaxel, mechlorethamine, cyclophosphamide, fluorouracil, thioguanine, carmustine, lomustine, melphalan, chlorambucil, streptozocin, methotrexate, vincristine, bleomycin, vinblastine, vindesine, dactinomycin, daunorubicin, doxorubicin, or tamoxifen), 5-hydroxytryptophan (serotonin) 3 (5-$HT_3$) receptor antagonists for the prevention and treatment of nausea and vomiting following chemotherapy (e.g., granisetron, ondansetron, or palonosetron), narcotics (e.g., morphine, meperidine, or codeine), antipsychotics including typical antipsychotics (e.g., haloperidol or fluphenazine) and atypical antipsychotics (e.g., risperidone, clozapine, olanzapine, or paliperidone), antiangiogenic agents (e.g., combrestatin, contortrostatin, or anti-vascular endothelial growth factor), polysaccharides, vaccines, antigens, DNA and other polynucleotides, antisense oligonucleotides, or siRNA.

The present semi-solid formulation described herein may also be applied to other locally acting active agents, such as astringents, antiperspirants, irritants, rubefacients, vesicants, sclerosing agents, caustics, escharotics, keratolytic agents, sunscreens and a variety of dermatologics including hypopigmenting and antipruritic agents.

Exemplary compositions of this semi-solid formulation described herein, and their uses, include:

(1) compositions containing local anesthetics, in combination with anti-inflammatory agents, antibiotics, or corticosteroids, for the prolonged local pain and inflammation relief, and for the prevention or treatment of infection (inhibition of microorganism growth).

(2) compositions containing 5-$HT_3$ receptor antagonists such as granisetron, ondansetron, palonosetron, and the like, for the prolonged prevention and treatment of nausea and vomiting following chemotherapy.

(3) compositions containing ophthalmic drugs, corticosteroid such as loteprednol for the treatment of inflammation of the eye; glaucoma drug such as brimonidine for the treatment of open-angle glaucoma or ocular hypertension; antiangiogenic agents such as combrestatin for the treatment of macular degeneration and retinal angiogenesis; and other compositions for the controlled release of ophthalmic drugs to the eye.

(4) compositions containing anti-inflammatory agents such as the NSAIDs, e.g., meloxicam, ibuprofen, naproxen, or COX-1 or COX-2 inhibitors, or glucocorticosteroids, for intra-articular injection.

(5) compositions containing antipsychotics including atypical antipsychotics such as risperidone, clozapine, olanzapine, paliperidone, and the like, and typical antipsychotics for the prolonged treatment of schizophrenia, schizoaffective disorder, the mixed and manic states of bipolar disorder, and irritability in autistic people.

The active agents may be present as the free base, or as an acid addition salt, or as a mixture thereof. A mixture of two different agents or a mixture of the same active agent in two forms, the free base form and the acid addition salt, may be used to achieve the desired pharmacological effect and release rate and duration.

The active agents (free base) can be readily converted into a salt with fatty acids and other pharmaceutically acceptable acids. Both saturated and unsaturated fatty acids such as lauric acid, myristic acid, palmitic acid, and oleic acid are natural fatty acids, and can be used. Other non-toxic organic acids such as pamoic acid can also be used. This conversion can increase its compatibility and solubility in the semi-solid vehicle. The selected active agents can be converted into a salt in advance before being incorporated into the semi-solid vehicle, or can be added into the semi-solid vehicle simultaneously at a 1:1 molar ratio or other molar ratios during the formulation manufacturing process.

The semi-solid injectable form of an active agent of the semi-solid formulation described herein may be prepared by mixing with the delivery vehicle already formed or directly mixed together with the main semi-solid lipid and the modifying excipients. The active agents may be first milled into fine particles before mixing with the other ingredients. The mechanical mixing process is performed at a suitable temperature to completely melt the semi-solid lipid and modifying excipients into a solution, and dissolve or mill by any mechanical means the active drugs into the delivery vehicle to from a clear solution or a homogeneous suspension, or use organic solvents to dissolve the active agent and the vehicle components. A vacuum may be applied to avoid air bubbles, and nitrogen may be applied to reduce oxidation of active drugs and the delivery vehicle components. After achieving a homogeneous and uniform pharmaceutical composition, the active agent semi-solid formulation can be cooled down to ambient temperature.

The amount of active agent(s) present in the composition can vary over a wide range depending on the a number of factors, such as the therapeutically effective dose of the active drug, the desired duration of biological or therapeutic effect, and the release profile of the composition. The concentration of the active agent may be in the range of about 0.01 to 60 wt %, preferably about 5 to 40 wt %, or more preferably about 10 to 40 wt %.

The concentration of the main semi-solid lipid may be in the range of about 1 to 99 wt %, preferably about 5 to 80 wt %. The concentration of the first modifying excipient may be in the range of about 1 to 50 wt %, preferably about 5 to 20 wt %. The concentrations of the second type of modifying excipients may be in the range of about 0.1 to 10 wt %, preferably about 0.5 to 5 wt %. In addition, other pharmaceutically acceptable agents such as antioxidants, preservatives, and other inert agents such as coloring or flavoring agents may be added.

This pharmaceutical semi-solid composition of the present semi-solid formulation described herein has a smooth non-tacky semi-solid paste. Therefore, the composition can be filled into syringes with a 21 gauge to 25 gauge needle for subcutaneous, subconjunctival, intradermal, intramuscular, epidural or intrathecal injection, or can also be conveniently applied onto already-open sites such as surgical wounds/site or exposed skin or mucous membrane.

After administration by injection or topical application, the active agent is release from the composition in a sustained and controlled manner. The rate of release may be regulated in a variety ways to accommodate the desired duration of therapeutic effect. For example, the rate may be increased or decreased by using different level of low solubility semi-solid lipid and different level of low solubility salts of the active agents with acids. It may also be altered by selecting different modifying excipients or by changing their amount, or the combination thereof. In addition, lower water solubility forms of active agents such as their base forms, or as complexes with fatty acids may be used to delay the release of active agents.

EXAMPLES

Example 1: Granisetron

Granisetron (1-methyl-N-((1R,3r,5S)-9-methyl-9-azabicyclo[3.3.1]nonan-3-yl)-1H-indazole-3-carboxamide) (KYTRIL®) is a serotonin 5-HT$_3$ receptor antagonist used as an antiemetic to treat nausea and vomiting following chemotherapy. Its main effect is to reduce the activity of the vagus nerve, which is a nerve that activates the vomiting center in the medulla oblongata. It does not have much effect on vomiting due to motion sickness. It does not have any effect on dopamine receptors or muscarinic receptors.

The solubility of active ingredients in the main single semi-solid lipid as a vehicle was determined, and potential suitable main single semi-solid lipids for the active ingredient were identified.

The solubility study was performed as follows. The targeted amount of active ingredient and the semi-solid lipid vehicle was weighed and transferred to a glass vial and sealed. The mixture was heated to about 90° C. in a water bath for about three minutes, and then vortexed for one minute. The procedure was repeated five times to completely dissolve all components and form a clear solution.

For solubility results, if the active ingredient is completely dissolved in the vehicle, the result is "completely soluble"; if there is minimal amount active ingredient particle left not dissolved, then the result is "almost completely soluble"; if part of the active ingredient is completely dissolved, then the result is "partially soluble" with an visual rough estimate of percentage of active ingredient dissolved (e.g., <50%, ~50%, or >50%); if only minimal amount active ingredient is dissolved or not soluble at all, then the result is "slightly soluble" or "insoluble".

The semi-solid formulations were cooled to ambient temperature. They appeared as a semi-transparent or opaque soft paste. Crystallization or precipitation of active ingredients was checked.

The solubility results were summarized in Table 1, which shows that the three single semi-solid lipid, S701, PGDS, and S645 can solubilize the targeted amount of granisetron (21 mg) in 0.5 gram of the vehicle.

TABLE 1

Solubility results for granisetron in single semi-solid lipid vehicle

| Sample ID | Semi-solid Lipid Vehicle | Vehicle Amount (g) | API Amount (mg) | Solubility Results |
|---|---|---|---|---|
| Granisetron F1 | S701 | 0.5 g | 21 mg | Completely soluble |
| Granisetron F2 | S378 | 0.5 g | 21 mg | Partially soluble (~80%) |
| Granisetron F3 | PGDS | 0.5 g | 21 mg | Almost completely soluble |
| Granisetron F4 | S645 | 0.5 g | 21 mg | Almost completely soluble |

The following formulations comprising granisetron were prepared.

Semisolid 001 Gran: [S701/Sup A (75/25)]/granisetron (96/4) or (96 wt %/4 wt %)

Semisolid 001 Gran PA: [S701/Sup A (75/25)]/granisetron PA (93/7)

Semisolid 001 Gran OA: [S701/Sup A (75/25)]/granisetron OA (93/7)

Semisolid 002 Gran: [PGDS/Sup A (70/30)]/granisetron (96/4)

Semisolid 003 Gran: [S645/Sup A (80/20)]/granisetron (96/4)

The semi-solid formulations were prepared by weighing the vehicle components and the drug into a glass vial, and closing the lid. S645 consists of caprylic/capric/isosteric/hydroxyl-steric/adipic glycerides, mixed esters; PGDS is polyglyceryl-2-diisostearate; S701 consists of ricinoleic acid partial glycerides; and Sup A consists of glycerides of $C_{12}$ to $C_{18}$ fatty acids. The vehicle components were melted by heating to 90° C. in a water bath, and granisetron was dissolved to form a clear solution and became a semi-transparent soft paste after cooling down to room temperature.

The solubility results for granisetron in semi-solid lipid formulations are shown in Table 2. Table 2 shows that all of the 4 semi-solid lipid vehicles (semi-solid lipid+modifying excipient) can solubilize the targeted amount of 25 mg granisetron or granisetron PA or OA in 0.5 gram of the vehicle.

TABLE 2

Solubility results for granisetron in semi-solid vehicle (semi-solid lipid + modifying excipient)

| Sample ID | Semi-solid Vehicle | Targeted Solubility (Granisetron/Vehicle) | Solubility Results |
|---|---|---|---|
| Semisolid 001 Gran | S701:Sup A (75:25) | 21 mg/0.5 g | Completely soluble |
| Semisolid 001 Gran PA | S701:Sup A (75:25) | (21 mg Gran + 17 mg PA)/0.5 g | Completely soluble |
| Semisolid 001 Gran OA | S701:Sup A (75:25) | (21 mg Gran + 19 mg OA)/0.5 g | Completely soluble |
| Semisolid 002 Gran | PGDS:Sup A (70:30) | 21 mg/0.5 g | Almost completely soluble |
| Semisolid 003 Gran | S645:Sup A (80:20) | 21 mg/0.5 g | Almost completely soluble |

For in vitro release determination, about 50 mg of the semi-solid formulation was weighed and enclosed in a porous semi-permeable membrane, and then placed into glass bottles with screw caps. 100 mL of 50 mM phosphate saline buffer (PBS), pH 7.4 was added to each bottle. The test bottles were transferred to a 37° C. oven without agitation. At various time points, bottles were removed and samples of about 1 mL were removed and analyzed for granisetron by light absorption at 206 nm. 50 mL of the buffer in each test bottle was removed and replaced with 51 mL of fresh buffer so that the PBS buffer in each bottle was maintained at 100 mL. The drug release profiles of the listed semi-solid formulations are summarized in the FIG. 1.

FIG. 1 showed granisetron and granisetron acid complex release from three different semi-solid compositions containing main semisolid lipid carrier with one modifying excipient. Semisolid 001 Gran, semisolid 002 Gran, and semisolid 003 Gran all contain approximately 4 wt % granisetron, and yielded similar granisetron release profile for about one week with about 20 to 30% drug released at 6 hour time point. Semisolid 001 Gran PA and semisolid 001 Gran OA both contain about the same 4 wt % granisetron excluding fatty acid, and approximately 7 wt % granisetron combined with palmitic acid or oleic acid, and yielded a slower, and better controlled release profile with about 16% and 14% drug released respectively after 6 hours.

Example 2: Loteprednol Etabonate

Loteprednol (chloromethyl 17-ethoxycarbonyloxy-11-hydroxy-10,13-dimethyl-3-oxo-7,8,9,11,12,14,15,16-octahydro-6H-cyclopenta[a]phenanthrene-17-carboxylate) (AL-REX® or LOTEMAX®) in the form of the ester loteprednol etabonate is a corticosteroid used in ophthalmology. Ocular applications for this drug include the treatment of inflammation of the eye due to allergies (according to the prescription information sheet), as well as chronic forms of keratitis (e.g., adenoviral or Thygeson's keratitis), vernal keratoconjunctivitis, pingueculitis, and episcleritis. The drug has little or no effect on intraocular pressure.

The solubility of loteprednol was measured and scored as described in Example 1. Table 3 shows that the 3 single semi-solid lipid, S701, PGDS, and S645 can solubilize the targeted amount of loteprednol etabonate (14 mg) in 0.5 gram of the vehicle.

TABLE 3

Solubility results for loteprednol etabonate in single semi-solid lipid vehicle

| Sample ID | Semi-solid Lipid Vehicle | Vehicle Amount (g) | API Amount (mg) | Solubility Results |
|---|---|---|---|---|
| Loteprednol F1 | S701 | 0.5 g | 14 mg | Completely soluble |
| Loteprednol F2 | S378 | 0.5 g | 14 mg | Partially soluble (~50%) |
| Loteprednol F3 | PGDS | 0.5 g | 14 mg | Almost completely soluble |
| Loteprednol F4 | S645 | 0.5 g | 14 mg | Almost completely soluble |

The following formulations comprising loteprednol etabonate were prepared.

Semisolid 001 Lote: [S701/Sup A (75/25)]/loteprednol (97/3)

Semisolid 001 Lote PA: [S701/Sup A (75/25)]/loteprednol PA (96/4)

Semisolid 001 Lote OA: [S701/Sup A (75/25)]/loteprednol OA (96/4)

Semisolid 002 Lote: [PGDS/Sup A (70/30)]/loteprednol (97/3)

Semisolid 003 Lote: [S645/Sup A (80/20)]/loteprednol (97/3)

The solubility results for loteprednol in semi-solid lipid formulations are shown in Table 4. Table 4 shows that all of the 4 semi-solid lipid vehicles (semi-solid lipid+modifying excipient) can solubilize the targeted amount of 14 mg loteprednol or granisetron PA or OA in 0.5 gram of the vehicle.

TABLE 4

Solubility results for loteprednol in semi-solid vehicle (semi-solid lipid + modifying excipient)

| Sample ID | Semi-solid Vehicle | Targeted Solubility (Loteprednol/Vehicle) | Solubility Results |
|---|---|---|---|
| Semisolid 001 Lote | S701:Sup A (75:25) | 14 mg/0.5 g | Completely soluble |
| Semisolid 001 Lote PA | S701:Sup A (75:25) | (14 mg Lote + 8 mg PA)/0.5 g | Completely soluble |
| Semisolid 001 Lote OA | S701:Sup A (75:25) | (14 mg Lote + 9 mg OA)/0.5 g | Completely soluble |
| Semisolid 002 Lote | PGDS:Sup A (70:30) | 14 mg/0.5 g | Almost completely soluble |
| Semisolid 003 Lote | S645:Sup A (80:20) | 14 mg/0.5 g | Almost completely soluble |

The semi-solid formulations were prepared by weighing the vehicle components and the drug into a glass vial, and closing the lid. S645 consists of caprylic/capric/isosteric/hydroxyl-steric/adipic glycerides, mixed esters; PGDS is polyglyceryl-2-diisostearate; S701 consists of ricinoleic acid partial glycerides; and Sup A consists of glycerides of $C_{12}$ to $C_{18}$ fatty acids. The vehicle components were melted by heating to 90° C. in a water bath, and loteprednol was dissolved to form a clear solution and became a semi-transparent soft paste after cooling down to room temperature.

For in vitro release determination, about 50 mg of each semi-solid formulation was weighed and enclosed in a porous semi-permeable membrane, and then placed into glass bottles with screw caps. 100 mL of 50 mM PBS, pH 7.4, was added to each bottle. The test bottles were transferred to a 37° C. oven without agitation. At various time points, bottles were removed and samples of about 1 mL were removed and analyzed for loteprednol etabonate by light absorption at 277 nm. 50 mL of the buffer in each test bottle was removed and replaced with 51 mL of fresh buffer so that the PBS buffer in each bottle was maintained at 100 mL.

Figure 2A:
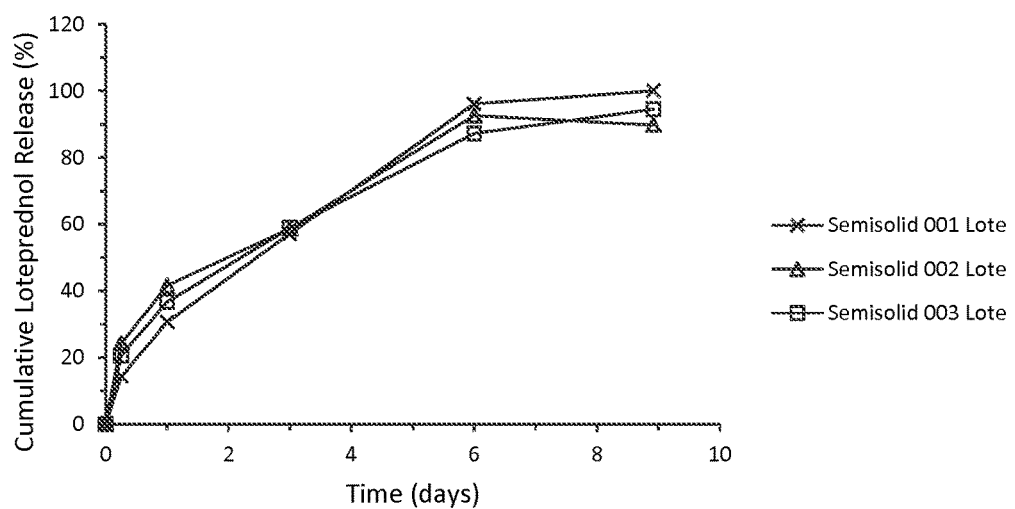
FIG. 2A shows loteprednol etabonate release from different semi-solid compositions containing one main semisolid lipid carrier with one modifying excipient: semisolid 001 Lote: [S701/Sup A (75/25)]/loteprednol (97/3); semisolid 002 Lote: [PGDS/Sup A (70/30)]/loteprednol (97/3); and semisolid 003 Lote: [S645/Sup A (80/20)]/loteprednol (97/3), all in 25 mM phosphate buffered saline, pH 7.4, 37° C.
Figure 2B:
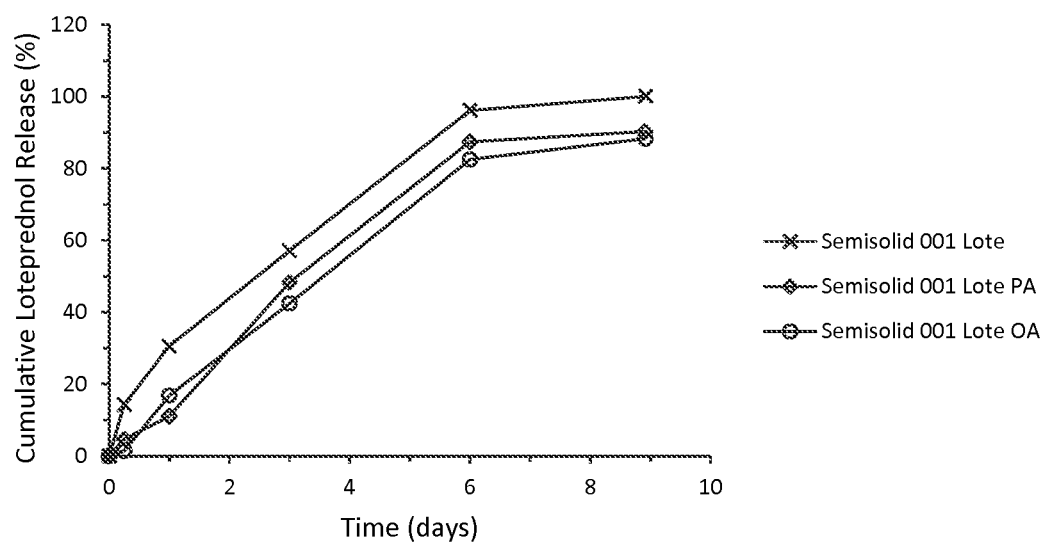
FIG. 2B shows loteprednol etabonate and loteprednol etabonate fatty acid complex release from semi-solid compositions containing main semisolid lipid carrier with one modifying excipient: semisolid 001 Lote: [S701/Sup A (75/25)]/loteprednol (97/3); semisolid 001 Lote PA: [S701/Sup A (75/25)]/loteprednol PA (96/4); and semisolid 001 Lote OA: [S701/Sup A (75/25)]/loteprednol OA (96/4), all in 25 mM phosphate buffered saline, pH 7.4, 37° C.

The drug release profiles of all the listed semi-solid formulations are summarized in the FIGS. 2A and 2B.

FIG. 2A showed loteprednol etabonate release from three different semi-solid compositions containing main semisolid lipid carrier with one modifying excipient. Semisolid 001 Lote, semisolid 002 Lote, and semisolid 003 Lote all contain approximately 3 wt % loteprednol etabonate, and yielded similar loteprednol etabonate release profile for about one week with about 14 to 24% drug released after 6 hours.

FIG. 2B showed loteprednol etabonate and loteprednol etabonate fatty acid complex release from the same semi-solid composition containing main semisolid lipid carrier with one modifying excipient. Semisolid 001 Lote, semisolid 001 Lote PA and semisolid 001 Lote OA all contain approximately 3 wt % loteprednol etabonate excluding fatty acid. For semisolid 001 Lote, about 14% loteprednol etabonate was released at 6 hour time point, while only 5% and 1% of loteprednol etabonate were released for semisolid 001 Lote PA and semisolid 001 Lote OA, respectively, after 6 hours.

Example 3: Meloxicam

Meloxicam (4-hydroxy-2-methyl-N-(5-methyl-2-thiazolyl)-2H-1,2-benzothiazine-3-carboxamide-1,1-dioxide) (MOBIC®) is a nonsteroidal anti-inflammatory drug (NSAID) with analgesic and fever reducer effects. It is a derivative of oxicam, closely related to piroxicam, and falls in the enolic acid group of nonsteroidal anti-inflammatory drugs (NSAIDs). Meloxicam starts to relieve pain about 30-60 minutes after administration.

The solubility of meloxicam was measured and scored as described in Example 1. Table 5 shows that none of the 4 single semi-solid lipid, S701, PGDS, S378 and S645 can solubilize the targeted amount of meloxicam (50 mg) in 0.5 gram of the vehicle. Therefore, it is not possible to prepare a semi-solid "solution" formulation for that dose level; however, it is still possible to prepare a homogeneous meloxicam semi-solid suspension formulation.

TABLE 5

Solubility results for meloxicam in single semi-solid lipid vehicle

| Sample ID | Semi-solid Lipid Vehicle | Vehicle Amount (g) | API Amount (mg) | Solubility Results |
| --- | --- | --- | --- | --- |
| Meloxicam F1 | S701 | 0.5 g | 50 mg | Partially soluble (<30%), formed nice semi-solid suspension |
| Meloxicam F2 | S378 | 0.5 g | 50 mg | Partially soluble (<30%), formed nice semi-solid suspension |
| Meloxicam F3 | PGDS | 0.5 g | 50 mg | Partially soluble (<30%), formed nice semi-solid suspension |
| Meloxicam F4 | S645 | 0.5 g | 50 mg | Partially soluble (<30%), formed nice semi-solid suspension |

The following formulations of meloxicam were prepared.

Semisolid 001 Melo: [S701/Sup A (75/25)]/meloxicam (91/9)

Semisolid 002 Melo: [S378 (100)]/meloxicam (91/9)

Semisolid 003 Melo: [PGDS/Sup A (70/30)]/meloxicam (91/9)

Semisolid 004 Melo: [S645/Sup A (80/20)]/meloxicam (91/9)

The solubility results for meloxicam in semi-solid lipid formulations are shown in Table 6. Table 6 shows that none of the four semi-solid lipid vehicles (semi-solid lipid+ modifying excipient) can solubilize the full targeted amount of meloxicam 50 mg in 0.5 gram of the vehicle. Therefore, meloxicam was prepared as homogeneous meloxicam semi-solid suspension formulations.

TABLE 6

Solubility results for meloxicam in semi-solid vehicle (semi-solid lipid + modifying excipient)

| Sample ID | Semi-solid Vehicle | Targeted Solubility (Meloxicam/ Vehicle) | Solubility Results |
| --- | --- | --- | --- |
| Semisolid 001 Melo | S701:Sup A (75:25) | 50 mg/0.5 g | Nice semi-solid suspension |
| Semisolid 002 Melo | S378 (100) | 50 mg/0.5 g | Nice semi-solid suspension |
| Semisolid 003 Melo | PGDS:Sup A (70:30) | 50 mg/0.5 g | Nice semi-solid suspension |
| Semisolid 004 Melo | S645:Sup A (80:20) | 50 mg/0.5 g | Nice semi-solid suspension |

The semi-solid formulations were prepared by weighing the vehicle components and the drug into a glass vial, and closing the lid. S378 are caprylic/capric/myristic/steric triglycerides; S645 are caprylic/capric/isosteric/hydroxyl-steric/adipic glycerides, mixed esters; PGDS are polyglyceryl-2-diisostearate; S701 are ricinoleic acid partial glycerides; and Sup A are glycerides of $C_{12}$ to $C_{18}$ fatty acids.

After heating to 90° C. in a water bath, both vehicle components were completely melted, and meloxicam was partially dissolved to form a yellowish solution with micronized meloxicam drug particles suspended. Upon cooling to room temperature, the cap was opened and excess moisture around the vial was wiped, and a stainless steel spatula was used to mix thoroughly to form a nice homogeneous soft paste suspension formulation.

For in vitro release determination, about 50 mg of each semi-solid formulation was weighed and enclosed in a porous semi-permeable membrane, and then placed into glass bottles with screw caps. 100 mL of 50 mM PBS, pH 7.4, was added to each bottle. The test bottles were transferred to a 37° C. oven without agitation. At various time points, bottles were removed and samples of about 1 mL were removed and analyzed for meloxicam by light absorption at 362 nm. 50 mL of the buffer in each test bottle was removed and replaced with 51 mL of fresh buffer so that the PBS buffer in each bottle was maintained at 100 mL.

Figure 3:
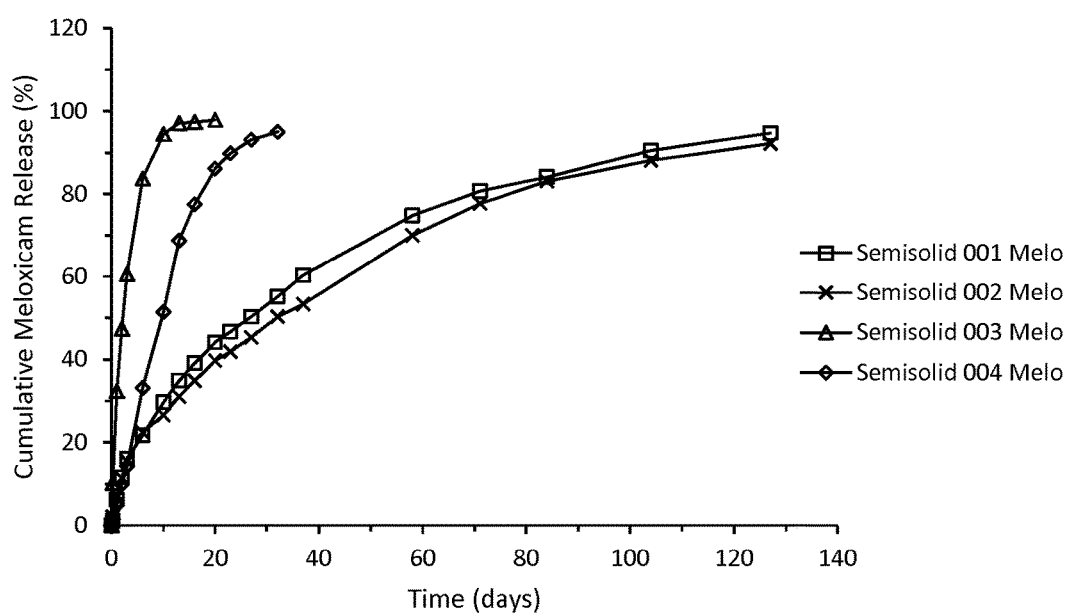
FIG. 3 shows meloxicam release from different semi-solid compositions containing one main semisolid lipid carrier with an without a modifying excipient: semisolid 001 Melo: [S701/Sup A (75/25)]/meloxicam (91/9); semisolid 002 Melo: [S378 (100)]/meloxicam (91/9); semisolid 003 Melo: [PGDS/Sup A (70/30)]/meloxicam (91/9); and semisolid 004 Melo: [S645/Sup A (80/20)]/meloxicam (91/9), all in 25 mM phosphate buffered saline, pH 7.4, 37° C.

The drug release profiles of all the listed semi-solid formulations are summarized in the FIG. 3.

FIG. 3 showed meloxicam release from four different semi-solid suspension formulation compositions containing main semisolid lipid carrier with one modifying excipient. Semisolid 001 Melo, semisolid 002 Melo, semisolid 003 Melo, and semisolid 004 Melo all contain approximately 9 wt % meloxicam, and yielded different meloxicam release profile ranging from about two weeks to more than four months. As the overall hydrophobicity of the formulation depots increased, their water solubility decreased, and thus resulted in slower dissolution rate and longer drug release duration.

Example 4: Risperidone

Risperidone (4-[2-[4-(6-fluorobenzo[d]isoxazol-3-yl)-1-piperidyl]ethyl]-3-methyl-2,6-diazabicyclo[4.4.0]deca-1,3-dien-5-one (RISPERDAL®, RISPERDAL CONSTA®, RISPERDAL M-TAB®, RISPERDAL QUICKLETS®) is an antipsychotic drug mainly used to treat schizophrenia (including adolescent schizophrenia), schizoaffective disorder, the mixed and manic states of bipolar disorder, and irritability in people with autism.

The solubility of risperidone was measured and scored as described in Example 1. Table 7 shows that none of the 4 single semi-solid lipid, S701, PGDS, S378 and S645 can solubilize the targeted amount of risperidone (25 mg) in 0.5 gram of the vehicle. Therefore, it is not possible to prepare a semi-solid "solution" formulation for that dose level with this hot-melt method.

TABLE 7

Solubility results for risperidone in single semi-solid lipid vehicle

| Sample ID | Semi-solid Lipid Vehicle | Vehicle Amount (g) | API Amount (mg) | Solubility Results |
|---|---|---|---|---|
| Risperidone F1 | S701 | 0.5 g | 25 mg | Partially soluble (~30%) |
| Risperidone F2 | S378 | 0.5 g | 25 mg | Partially soluble (~30%) |
| Risperidone F3 | PGDS | 0.5 g | 25 mg | Partially soluble (~30%) |
| Risperidone F4 | S645 | 0.5 g | 25 mg | Partially soluble (~30%) |

A formulation of risperidone was prepared as follows: Semisolid 001 Risp PA: [S701/Sup A (90/10)]/risperidone PA (90/10).

This formulation was prepared by solvent evaporation method. Both vehicle components and risperidone were weighed and transferred into a glass vial. S701 consists of ricinoleic acid partial glycerides; and Sup A consists of glycerides of $C_{12}$ to $C_{18}$ fatty acids. About 3 mL acetone was added, and the vial was sealed and vortexed for about 5 minutes until risperidone was dissolved. The vial was opened, and placed in a hood for 4 hours to remove the solvent, then heated at about 50° C. (slightly yellowish clear solution) under vacuum for about 8 hours to remove the solvent. The drug risperidone partially precipitated out after cooling down to room temperature, and this risperidone semi-solid formulation became a nice smooth homogeneous soft paste suspension formulation.

The solubility results for risperidone in semi-solid lipid formulations are shown in Table 8. Table 8 shows that none of the 4 semi-solid lipid vehicles (semi-solid lipid+modifying excipient) can solubilize the full targeted amount of meloxicam 50 mg in 0.5 gram of the vehicle. Therefore, risperidone was prepared as very smooth semi-solid suspension formulations by solvent-evaporation method.

TABLE 8

Solubility results for risperidone in semi-solid vehicle (semi-solid lipid + modifying excipient)

| Sample ID | Semi-solid Vehicle | Targeted Solubility (Risperidone/Vehicle) | Solubility Results |
|---|---|---|---|
| Semisolid 001 Risp PA | S701:Sup A (90:10) | (25 mg Risp + 23 mg PA)/0.5 g | Completely soluble |
| Semisolid 002 Risp | S378 (100) | 25 mg/0.5 g | Partially soluble (~30%) |
| Semisolid 003 Risp | PGDS:Sup A (70:30) | 25 mg/0.5 g | Partially soluble (~30%) |
| Semisolid 004 Risp | S645:Sup A (80:20) | 25 mg/0.5 g | Partially soluble (~30%) |

For in vitro release determination, about 50 mg of the semi-solid formulation was weighed and enclosed in a porous semi-permeable membrane, and then placed into a glass bottle with a screw cap. 100 mL of 50 mM PBS, pH 7.4, was added to the bottle. The test bottle was transferred to a 37° C. oven without agitation. At various time points, bottle was removed and samples of about 1 mL were removed and analyzed for risperidone by light absorption at 246 nm. 50 mL of the buffer in the test bottle was removed and replaced with 51 mL of fresh buffer so that the PBS buffer in each bottle was maintained at 100 mL.

Figure 4:
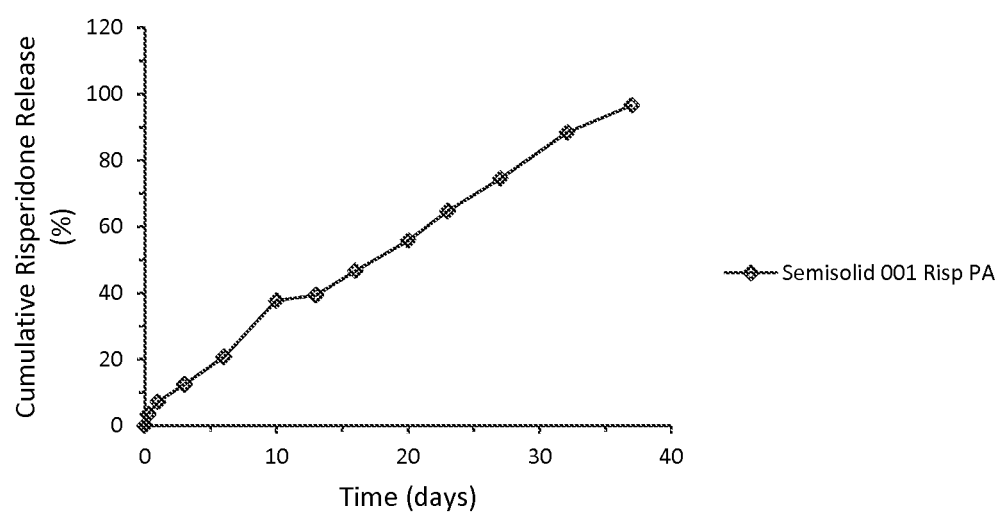
FIG. 4 shows risperidone release from a semi-solid composition containing a main semisolid lipid carrier and a modifying excipient: semisolid 001 Risp PA: [S701/Sup A (90/10)]/risperidone PA (90/10), in 25 mM phosphate buffered saline, pH 7.4, 37° C.

The drug release profiles of the semi-solid formulations are summarized in the FIG. 4.

FIG. 4 showed risperidone release from one semi-solid composition containing main semisolid lipid carrier with one modifying excipient. Semisolid 001 Risp PA contains approximately 10 wt % risperidone combining with palmitic acid, and yielded a linear (zero-order release kinetics) drug release profile for more than five weeks.

Example 5: Latanoprost

Latanoprost (XALATAN®) is used for treating glaucoma or ocular hypertension by reducing intraocular pressure.

The solubility of latanoprost was measured and scored as described in Example 1. Table 9 shows that all of the four single semi-solid lipids, S701, PGDS, S378 and S645 can solubilize the targeted amount of latanoprost 25 mg in 0.5 gram of the vehicle.

TABLE 9

Solubility results for latanoprost in single semi-solid lipid vehicle

| Sample ID | Semi-solid Lipid Vehicle | Vehicle Amount (mg) | API Amount (mg) | Solubility Results |
|---|---|---|---|---|
| Latanoprost F1 | S701 | 500 mg | 25 mg | Completely soluble |
| Latanoprost F2 | S378 | 250 mg | 12.5 mg | Completely soluble |
| Latanoprost F3 | PGDS | 250 mg | 12.5 mg | Completely soluble |
| Latanoprost F4 | S645 | 250 mg | 12.5 mg | Completely soluble |

The following formulations of latanoprost were prepared as in Example 1.
Semisolid 001 Lata: [S701/Sup A (90/10)]/latanoprost (95/5) or (95 wt %/5 wt %)
Semisolid 002 Lata: [S378 (100)]/latanoprost (95/5)
Semisolid 003 Lata: [PGDS/Sup A (70/30)]/latanoprost (95/5)
Semisolid 004 Lata: [S645/Sup A (80/20)]/latanoprost (95/5)

The solubility results for latanoprost in semi-solid lipid formulations are shown in Table 10. Table 10 shows that all of the 4 semi-solid lipid vehicles (semi-solid lipid plus modifying excipient) can solubilize the targeted amount of 25 mg latanoprost in 0.5 gram of the vehicle.

TABLE 10

Solubility results for latanoprost in semi-solid vehicle (semi-solid lipid plus modifying excipient)

| Sample ID | Semi-solid Vehicle | Targeted Solubility (Latanoprost/Vehicle) | Solubility Results |
|---|---|---|---|
| Semisolid 001 Lata | S701:Sup A (90:10) | 25 mg/0.5 g | Completely soluble |
| Semisolid 002 Lata | S378 (100) | 25 mg/0.5 g | Completely soluble |
| Semisolid 003 Lata | PGDS:Sup A (70:30) | 25 mg/0.5 g | Completely soluble |
| Semisolid 004 Lata | S645:Sup A (80:20) | 25 mg/0.5 g | Completely soluble |

Figure 5A:
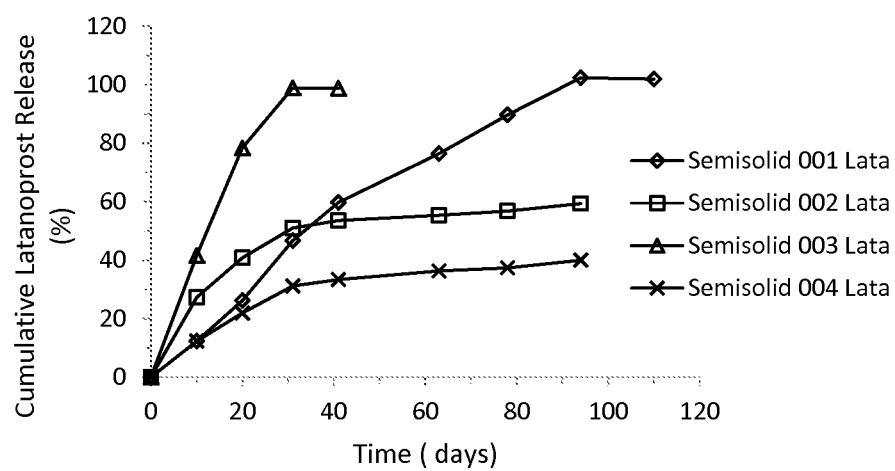
FIG. 5A shows latanoprost release from different semi-solid compositions containing one main semisolid lipid carrier with one modifying excipient: semisolid 001 Lata: [S701/Sup A (90/10)]/latanoprost (95/5); semisolid 002 Lata: [S378 (100)]/latanoprost (95/5); semisolid 003 Lata: [PGDS/Sup A (70/30)]/latanoprost (95/5); and semisolid 004 Lata: [S645/Sup A (80/20)]/latanoprost (95/5), all in 25 mM phosphate buffered saline, pH 7.4, 37° C.

FIG. 5A showed latanoprost release from four different semi-solid compositions containing one main semisolid lipid carrier with one modifying excipient. Semisolid composition from semisolid 001 Lata to semisolid 004 Lata containing approximately 5 wt % latanoprost showed a good controlled release from about a month to three months. All four semisolid compositions employed one major semi-solid lipid with a modifying lipid. As the overall hydrophobicity of the formulation depots increase, their water solubility decrease, and thus resulting slower dissolution rate and longer drug release duration. Semisolid 001 Lata and semisolid 003 Lata yielded about very linear three month and one month drug release; while semisolid 003 Lata and semisolid 004 Lata yielded about one month drug release, then followed by very slow release.

Figure 5B:
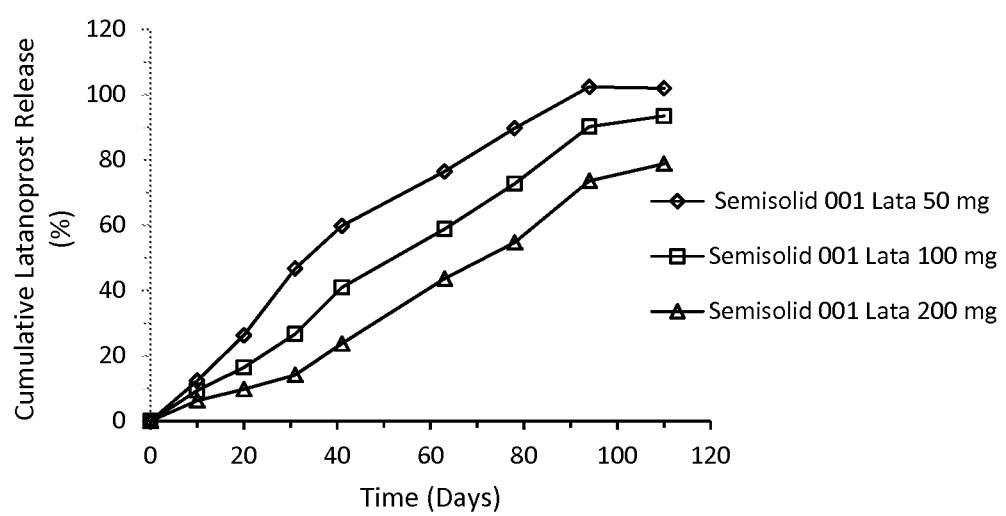
FIG. 5B shows latanoprost release from different semi-solid compositions: semisolid 001 Lata: [S701/Sup A (90/10)]/latanoprost (95/5), in 25 mM phosphate buffered saline, pH 7.4, 37° C.

FIG. 5B showed latanoprost release from three different amounts (50, 100, and 200 mg) of a semi-solid formulation, semisolid 001 Lata: [S701/Sup A (90/10)]/Latanoprost (95/5). As the amounts/volumes of the formulation increases, the release rate of latanoprost relative to the total drug loading decreased as it take longer time for the drug to diffuse out and the vehicle to erode, and thus the total drug release duration is also longer.

Example 6: Viscosity

The viscosity of the semi-solid formulations were determined on a calibrated Brookfield RVDV-I Prime CP model viscometer using cone spindle CPE-51. The semi-solid formulation samples stored in sealed glass vials were first heated to about 40° to 50° C. in an oven until the samples became a flowable viscous liquid. Then approximately 0.3 gram of each sample was weighed into the center of the warmed sample cup. Bubbles were avoided when possible. The sample cup was attached to the viscometer, and the viscosity was measured at an appropriate speed of rotation so that the % torque is between 10% and 100%. The viscosity and % torque at the target temperature were recorded. Due to the soft paste nature of these materials at room temperature, the viscosity of semi-solid formulations was determined at 30° C. at that point the semi-solid formulations become a flowable viscous liquid/semi-solid under pressure.

The viscosity values for the main semi-solid lipid are relatively low, typically below 1000 cPs at 30° C., except for S645, which is a very viscous liquid. The viscosity values of the four main semi-solid components were determined at 30° C. and summarized in Table 11.

TABLE 11

Viscosity values of the main semi-solid lipid

| Sample ID | Viscosity (cP) at 30° C. |
|---|---|
| S378 neat | 45 |
| S701 neat | 563 |
| PGDS neat | 427 |
| S645 neat | 2454 |

The semi-solid drug delivery vehicle typically contains two or more components, the main semi-solid component with one or two modifying excipients. The overall semi-solid vehicle typically exhibits even lower viscosity, since the modifying excipient often acts as a waxy lubricant, thus further reducing the viscosity of semi-solid vehicle when compared with the main semi-solid component. The viscosity values for the four main components modified with 10 wt % to 30 wt % of Sup A were determined and summarized in Table 12.

TABLE 12

Viscosity values for the overall semi-solid vehicle (main semi-solid lipid + modifying excipient)

| Sample ID | Viscosity (mPa · s) at 30° C. |
|---|---|
| S701:Sup A (75:25) | 295 |
| S701:Sup A (90:10) | 427 |
| PGDS:Sup A (70:30) | 191 |
| S645:Sup A (80:20) | 1028 |

For the first main semi-solid lipid S378, the viscosity was very low viscosity at about 50 cPs before being modified with any modifying excipient. For the main semi-solid lipid S701, the viscosity of the overall semi-solid vehicle reduced from 563 cPs (for neat S701) to 427 cPs and 295 cPs respectively after being modified with 10 wt % and 25 wt % of Sup A. For the 3rd main semi-solid lipid PGDS, the viscosity of the overall semi-solid vehicle reduced from 427 cPs (for neat PGDS) to 191 cPs after being modified with 30 wt % of Sup A. For the 4th main semi-solid lipid S645, the viscosity of the overall semi-solid vehicle reduced from 2454 cPs (for neat S645) to 1028 cPs (58% reduction of viscosity) after being modified with 20 wt % of Sup A.

The viscosity results for the semi-solid formulations listed in the in vitro release study were summarized in Table 13. The viscosity value of these semi-solid formulations ranges from 55 cPs to 1168 cPs, with the majority of them below 500 cPs at 30° C. The overall semi-solid formulations exhibited very lower viscosity.

TABLE 13

Viscosity results for semi-solid formulations

| Sample ID | Semi-solid Formulation Composition | Viscosity (mPa · s) at 30° C. |
|---|---|---|
| Semisolid 001 Gran | [S701/Sup A (75/25)]/Granisetron (96/4) | 378 |
| Semisolid 001 Gran PA | [S701/Sup A (75/25)]/Granisetron PA (93/7) | 359 |
| Semisolid 001 Gran OA | [S701/Sup A (75/25)]/Granisetron OA (93/7) | 349 |
| Semisolid 002 Gran | [PGDS/Sup A (70/30)]/Granisetron (96/4) | 239 |
| Semisolid 003 Gran | [S645/Sup A (80/20)]/Granisetron (96/4) | 1162 |
| Semisolid 001 Lote | [S701/Sup A (75/25)]/Loteprednol (97/3) | 326 |
| Semisolid 001 Lote PA | [S701/Sup A (75/25)]/Loteprednol PA (96/4) | 323 |
| Semisolid 001 Lote OA | [S701/Sup A (75/25)]/Loteprednol OA (96/4) | 310 |
| Semisolid 002 Lote | [PGDS/Sup A (70/30)]/Loteprednol (97/3) | 220 |
| Semisolid 003 Lote | [S645/Sup A (80/20)]/Loteprednol (97/3) | 1168 |
| Semisolid 001 Risp PA | [S701/Sup A (90/10)]/Risperidone PA (90/10) | 437 |
| Semisolid 001 Lata | [S701/Sup A (90/10)]/Latanoprost (95/5) | 458 |
| Semisolid 002 Lata | [S378]/Latanoprost (95/5) | 55 |
| Semisolid 003 Lata | [PGDS/Sup A (70/30)]/Latanoprost (95/5) | 205 |
| Semisolid 004 Lata | [S645/Sup A (80/20)]/Latanoprost (95/5) | 1058 |

Once the active ingredient, granisetron, loteprednol etabonate, or latanoprost, was incorporated into the final semi-solid drug delivery vehicle through a hot melt process the mixture formed a semi-solid solution formulation with the active drug molecularly dispersed in the semi-solid vehicle media. The active drugs only slightly increase the viscosity of the semi-solid formulations when compared with the semi-solid vehicle. As the drug (solid powder) loading increases, the soft semi-solid paste formulation can change to a relatively hard semi-solid paste formulation, thus resulting in increased viscosity.

For the active ingredient risperidone, since this drug can't be incorporated into the semi-solid vehicle by the hot melt process, the semi-solid formulation was prepared by solvent evaporation process instead.

For the active ingredient meloxicam, since this drug can't be incorporated into the semi-solid vehicle by the hot melt process, or be incorporated by solvent evaporation process with a volatile solvent, so the meloxicam semi-solid formulations were prepared as a homogenous suspension semi-solid formulation using micronized meloxicam drug, and their viscosities were not determined. However, all four semi-solid suspension formulations using S378, S701, PGDS and S645 as the main semi-solid lipid components are readily injectable with 21 gauge needles.

All the listed semi-solid formulations for in vitro release study using S378, S701, and PGDS as the main semi-solid lipid with the viscosity ranging from 55 cPs to 500 cPs at 30° C. are readily injectable with 23 gauge needles, while the three semi-solid formulations using S645 as the main semi-solid lipid are readily injectable with 21 gauge needles (still injectable with a 23 gauge needle with some resistance).

What is claimed:

1. A pharmaceutical composition, comprising
   i. a first glyceride mixture comprising one or more glycerides selected from the group consisting of (a) polyglyceryl-2-diisostearate; (b) a mixture of caprylic, capric, myristic, and stearic triglycerides; (c) bis-diglyceryl polyacyladipate-1; (d) glyceryl ricinoleate; (e) a mixture of triglycerides, diglycerides and monoglycerides of C10-C18 fatty acids; and (f) triglycerides of saturated C12-C18 fatty acids; and
   ii. meloxicam, or a fatty acid complex thereof, at a concentration of 5 to 60 wt % in the first glyceride mixture;

wherein the pharmaceutical composition consists of a homogenous semi-solid suspension, wherein the semi-solid suspension consists of a soft paste with a viscosity of 50-2000 cPs at 30° C., and wherein the semi-solid suspension forms a depot that releases meloxicam for over two weeks when measured in vitro at 37° C.

2. The pharmaceutical composition of claim 1, further comprising a second glyceride mixture consisting of one or more glycerides selected from the group consisting of (a) a mixture of caprylic, capric, myristic, and stearic triglycerides; (b) glyceryl ricinoleate; (c) a mixture of triglycerides, diglycerides and monoglycerides of C10-C18 fatty acids; and (d) triglycerides of saturated C12-C18 fatty acids, wherein the second glyceride mixture has a lower or higher hydrophilic-lipophilic balance (HLB) than the first glyceride mixture, wherein meloxicam is released from the depot for over two weeks when measured in vitro at 37° C.

3. The pharmaceutical composition of claim 2, wherein the concentration of the second glyceride mixture is 1-50 wt % of the pharmaceutical composition.

4. A method for treating a disease or disorder comprising locally administering the pharmaceutical composition of claim 1 by subcutaneous, intramuscular, or intraperitoneal injection.

5. The method of claim 4, wherein the-injection is by a 21 gauge to 27 gauge needle.

6. A method of manufacturing a pharmaceutical composition, comprising
   i selecting-a first glyceride mixture comprising one or more glycerides selected from the group consisting of (a) polyglyceryl-2-diisostearate; (b) a mixture of caprylic, capric, myristic, and stearic triglycerides; (c) bis-diglyceryl polyacyladipate-1; (d) glyceryl ricinoleate; (e) a mixture of triglycerides, diglycerides and monoglycerides of C10-C18 fatty acids; and (f) triglycerides of saturated C12-C18 fatty acids; and
   ii homogeneously mixing meloxicam in the semi-solid mixture to 5 to 60 wt % of the pharmaceutical composition;

wherein the pharmaceutical composition consists of a homogenous semi-solid suspension, wherein the semi-solid suspension consists of a soft paste with a viscosity of 50-2000 cPs at 30° C., and wherein the semi-solid suspension forms a depot that releases meloxicam for over two weeks when measured in vitro at 37° C.

7. The process of claim 6, further comprising
iii measuring the release kinetics and duration of meloxicam from the semi-solid mixture of step iii in vitro at 37° C., and
iv mixing the product of step iii with a second glyceride mixture comprising one or more glycerides selected from the group consisting of (a) a mixture of caprylic, capric, myristic, and stearic triglycerides; (b) glyceryl ricinoleate; (c) a mixture of triglycerides, diglycerides and monoglycerides of C10-C18 fatty acids; and (d) triglycerides of saturated C12-C18 fatty acids, wherein the second glyceride mixture has a lower or higher HLB (hydrophobicity) than the first glyceride mixture, and wherein meloxicam is released from the depot for over two weeks.

* * * * *